(12) United States Patent
Reinwand et al.

(10) Patent No.: US 6,430,252 B2
(45) Date of Patent: Aug. 6, 2002

(54) X-RAY COMPUTED TOMOGRAPHY APPARATUS

(75) Inventors: Mario Reinwand, Steinbach; Karl Stierstorfer, Erlangen, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/912,137

(22) Filed: Jul. 25, 2001

(30) Foreign Application Priority Data

Jul. 25, 2000 (DE) .......................... 100 36 142

(51) Int. Cl.⁷ ............................... A61B 6/03
(52) U.S. Cl. ................. 378/8; 378/9; 378/901
(58) Field of Search ............. 378/4, 8, 19, 901

(56) References Cited

U.S. PATENT DOCUMENTS 5,953,444 A  9/1999 Joseph et al. ............... 382/131

2002/0018540 A1 * 2/2002 Stierstorfer ................. 378/16

OTHER PUBLICATIONS

"A comparative Study of Two Postreconstruction Beam Hardening Correction Methods," Herman et al., IEEE Trans. on Med. Imaging, vol. MI/2, No. 3 (1983) pp. 128–135.

* cited by examiner

*Primary Examiner*—David V. Bruce
(74) *Attorney, Agent, or Firm*—Schiff Hardin & Waite

(57) ABSTRACT

In an X-ray computed tomography apparatus with retrospective beam hardening correction, an overall image of a body slice under examination is determined from overall attenuation values that are obtained from the body slice. At least one partial image that shows essentially only one body substance, such as bone substance, is extracted from this overall image. Attenuation partial values are employed for determining a correction value. The attenuation values are determined for each overall attenuation value from the at least one partial image by re-projection. A correction value is derived from the beam hardening error that is determined for a material combination of two different reference materials.

7 Claims, 1 Drawing Sheet

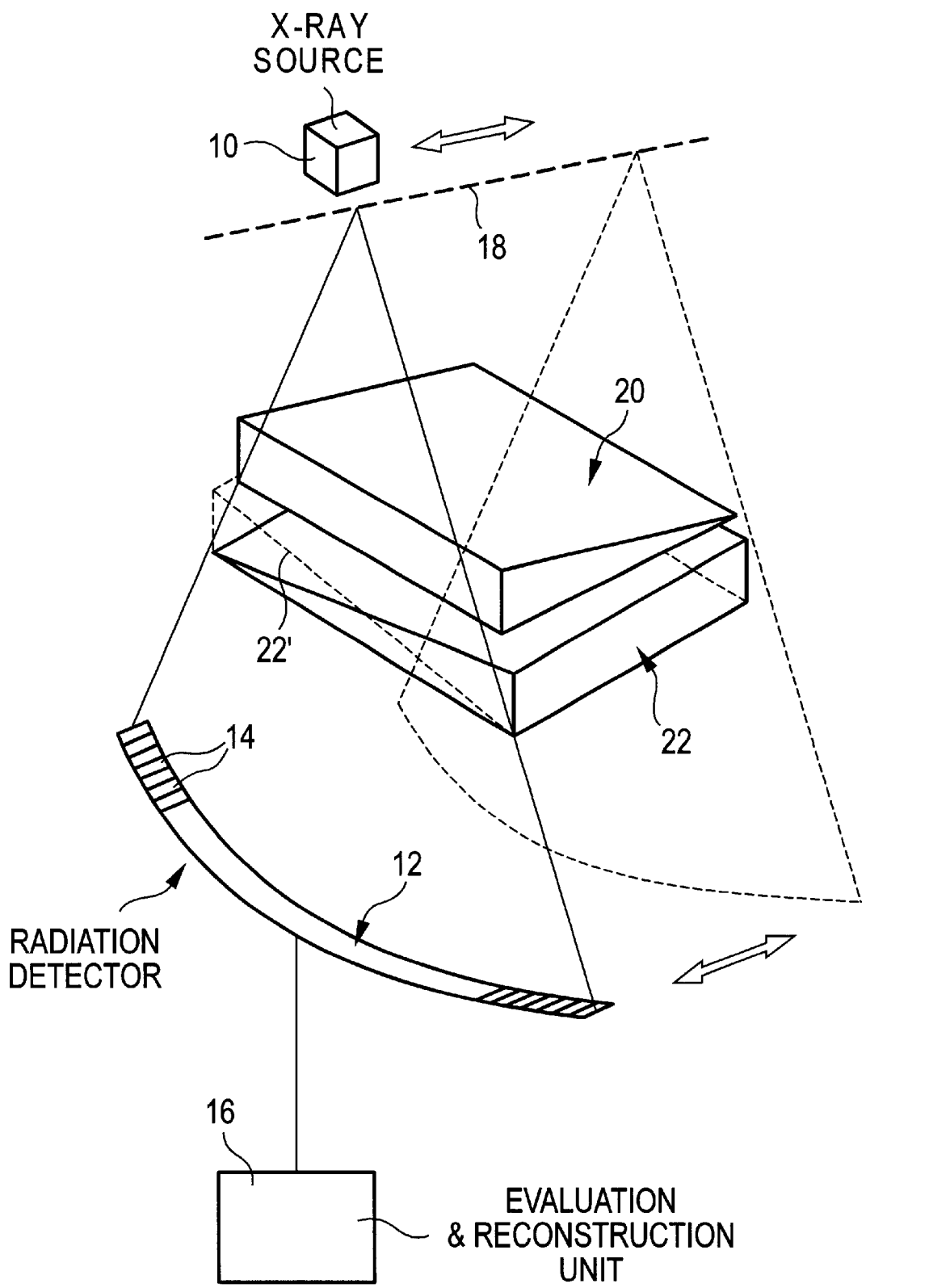

X-RAY COMPUTED TOMOGRAPHY APPARATUS

BACKGROUND OF THE INVENTION

1. Field of the Invention

The present invention is directed to beam-hardening correction in an X-ray computer tomography apparatus.

2. Description of the Prior Art

In X-ray computed tomography, a shift of the average energy of the X-rays toward higher values occurs as a consequence of the polychromatic spectrum of the radiation emitted by the X-ray source and as a consequence of the energy-dependent absorption of the X-rays in the body of the patient under examination. This effect is called beam hardening. This effect becomes more pronounced as the transirradiated path in the body becomes longer. In the reconstructed image of the transirradiated body slice, this beam-hardening effect leads to unwanted image artifacts that negatively affect the precise medical interpretation of the image.

Standard algorithms (for instance, polynomial correction) are known for the correction of such image artifacts caused by beam hardening. These produce satisfactory results as long as the spectral absorption or attenuation behavior of the transirradiated body substances does not significantly differ from the spectral attenuation behavior of a reference substance for which the correction algorithm was developed. Water is used as the reference substance in the standard case since water exhibits a spectral attenuation behavior comparable to soft tissue in the human body and the human body is largely composed of soft tissue. Beam-hardening errors then can be eliminated to a significant extent in body regions where essentially only soft tissue is encountered. When, however, the X-rays also passes through bone tissue, the algorithm is no longer accurate since bone tissue exhibits a spectral attenuation behavior that deviates substantially from water. The same is also true, for example, of vessels filled with contrast agent. Since the extent to which soft tissue and bone tissue were responsible for the beam attenuation is initially unknown for the measured values acquired in the course of the examination of a patient, a satisfactory beam hardening correction is not possible based solely on knowledge of the measured values.

Methods referred to as retrospective correction methods were therefore developed wherein an overall image of the transirradiated body slice is first reconstructed from the measured, overall attenuation values, and this overall image is subsequently analyzed and resolved into sub-images. Each of the sub-images shows only a part of the various body substances. In the standard case, a bone image and a soft tissue image are generated. Partial attenuation values that indicate the beam attenuation by the appertaining part of the body substances, i.e., for example, bone tissue or soft tissue, are then calculated from the individual sub-images by re-projection. Subsequently, correction values that are added to the originally measured overall attenuation values are determined for the partial attenuation values of each sub-image. For example, the correction values are taken from correction characteristics that were separately determined in advance for the respective body substances on the basis of reference materials with comparable attenuation. An overall image—which is now corrected for beam hardening—of the transirradiated body slice is reconstructed a second time from the corrected, overall attenuation values.

More detailed information about retrospective (post construction) correction methods may be found, for example, in "A Comparative Study of two Postreconstruction Beam Hardening Correction Methods" by G. T. Herman, S. S. Trivedi, IEEE Transactions on Medical Imaging, MI-2, 1983, pp. 128 ff., and in "A Method for Correcting Bone Induced Artifacts in Computer Tomography Scanners" by P. M. Joseph, R. D. Spital, Journal of Computer Assisted Tomography, No. 2, 1978, pp. 100 ff.

It has been shown in practice that the known retrospective correction methods can in fact clearly reduce image artifacts caused by beam hardening compared to traditional, standard algorithms, however, image artifacts continue to be observed and elimination or at least reduction thereof is desirable.

SUMMARY OF THE INVENTION

An object of the present invention is to provide a computed tomography apparatus with improved beam-hardening correction.

In a first version of the solution, this object is achieved in an X-ray computed tomography apparatus constructed and operating as follows.

A radiator/detector arrangement supplies a set of measured intensity values for each X-ray projection of a body slice of a patient under examination, each measured value thereof being representative of the intensity of the X-rays that have passed through the body slice in a respective partial projection region of the overall projection region. An electronic evaluation and reconstruction unit is connected to the radiator/detector arrangement and is configured for a) determining an overall attenuation value for each measured intensity value, the overall attenuation value being representative of the actual overall attenuation of the X-rays produced in the body slice in the appertaining partial projection region;

b) reconstructing an overall image of the body slice proceeding from the overall attenuation values;

c) extracting a first partial image from this overall image wherein essentially only those image parts of the overall image are contained that correspond to a first part of the various substances occurring in the body slice;

d) determining respective first attenuation partial values allocated respectively to each overall attenuation value on the basis of this first partial image, the first attenuation partial value being a criterion for the attenuation that the X-rays experiences in the respective projection partial region due to the first part of the substances;

e) extracting a second partial image from the overall image of the body slice wherein essentially only those image parts of the overall image are contained that correspond to a second part of the substances in the body slice differing from the first part;

f) determining respective, second attenuation partial values on the basis of this second partial image allocated respectively to each overall attenuation value, the second attenuation sub-value being a criterion for the attenuation that the X-radiation experiences in the respective projection partial region due to the second part of the substances;

g) determining a correction value for every overall attenuation value on the basis of previously determined beam-hardening correction information stored in the evaluation and reconstruction unit and dependent on the two attenuation partial values; and h) determining an overall attenuation value corrected for beam hardening for each overall attenuation value according to the following equation:

$$g_{corr} = g + k(t_1, t_2) \quad (1),$$

wherein g is the overall attenuation value, $g_{corr}$ is the overall attenuation value corrected for beam hardening, $t_1$ is the first attenuation partial value, $t_2$ is the second attenuation partial value and $k(t_1, t_2)$ is the correction value dependent on $t_1$ and $t_2$.

For determining the beam hardening correction information, in accordance with the invention a set of reference overall attenuation values $g_{ref}(s_1, s_2)$ is determined for a material combination of a first reference material and a second reference material different therefrom. This set of reference overall attenuation values $g_{ref}(s_1, s_2)$ is representative of the actual overall attenuation of the X-rays produced by this material combination at various respective thicknesses of the first material and the second reference material. For this determination, $s_1$ references a first individual attenuation value that is representative of the theoretical linear attenuation of the X-rays by the first reference material for the respective thickness of the first reference material, and $s_2$ references a second individual attenuation value that is representative of the theoretical linear attenuation of the X-rays by the second reference material for the respective thickness of the second reference material. The evaluation and reconstruction unit determines (and uses) the aforementioned correction according to the following equation:

$$k(t_1, t_2) = t_1 + t_2 - g_{ref}(s_1 = t_1, s_2 = t_2) \quad (2).$$

In an alternative, second version, the inventive X-ray computed tomography apparatus is constructed and operates as follows:

A radiator/detector arrangement supplies a set of measured intensity values for each X-ray projection of a body slice of a patient under examination, each measured value thereof being representative of the intensity of the X-rays that have passed through the body slice in a respective partial projection region of the overall projection region. An electronic evaluation and reconstruction unit is connected to the radiator/detector arrangement and is configured for a) determining an overall attenuation value for each measured intensity value, this overall attenuation value being representative of the actual overall attenuation of the X-rays produced in the body slice in the appertaining partial projection region;

b) reconstructing an overall image of the body slice proceeding from the overall attenuation values;

c) extracting a partial image from this overall image wherein essentially only those image parts of the overall image are contained that correspond to a first part of the various substances occurring in the body slice;

d) determining respective attenuation partial values allocated respectively to each overall attenuation value on the basis of this partial image, the attenuation partial values being a criterion for the attenuation that the X-rays experiences in the respective projection partial region due to the first part of the substances;

e) determining a correction value for every overall attenuation value on the basis of previously determined beam-hardening correction information stored in the evaluation and reconstruction unit and dependent on the respective attenuation sub-value; and f) determining an overall attenuation value corrected for beam hardening for each overall attenuation value according to the following equation:

$$g_{corr} = g + k(t) \quad (3),$$

wherein g is the overall attenuation value, $g_{corr}$ is the overall attenuation value corrected for beam hardening, and $k(t)$ is the correction value dependent on t.

For determining the beam hardening correction information in the second version of the invention, a set of reference overall attenuation values $g_{ref}(s_1, s_2)$ is determined for a material combination of a first reference material and a second reference material different therefrom. This set of reference overall attenuation values $g_{ref}(s_1, s_2)$ is representative of the actual overall attenuation of the X-rays produced by this material combination at various respective thicknesses of the first material and the second reference material. For this determination $s_1$ is a first individual attenuation value that is representative of the theoretical linear attenuation of the X-rays by the first reference material for the respective thickness of the first reference material, and $s_2$ references a second individual attenuation value that is representative of the theoretical linear attenuation of the X-rays by the second reference material for the respective thickness of the second reference material. The evaluation and reconstruction unit is configured for determining (and using) the overall attenuation value dependent on the reference overall attenuation values according to the following equation applies:

$$k(g, t) = t + s_2 - g_{ref}(s_1 = t, s_2) \quad (4),$$

wherein $$g_{ref}(s_1 = t, s_2) = g \quad (5)$$

applies for $g_{ref}(s_1 = t, s_2)$.

The two versions have in common the use of a correction value that takes the attenuation by a combination of two different materials into consideration. It has been shown in the human body that the beam hardening by one substance (for instance, bone tissue) is not independent of whether other substances (for instance, soft tissue) are additionally present in the beam path. However, the known retrospective correction methods are based precisely on the premise that this precondition of independency exits, by taking only the attenuation by a single (generalized) substance into consideration. By employing a correction value dependent on the attenuation of two materials, it is possible to come very close to the actual conditions in the human body. Images that are very low in disturbing image artifacts thus can be generated, particularly given exposures of body regions having a comparatively high proportion of bone.

Materials whose spectral attenuation behavior is similar to the body substances that are to be taken into consideration in the partial images are expediently selected as the reference materials. For a partial image that should essentially show only soft tissue, it is expedient to select water as reference material. For a partial image that should essentially show only bone substance, for example, a mixture of $K_2HPO_4$ and water can be selected as reference material (S.C.E. Cann, Radiology 166, pp. 509–522 (1988)).

DESCRIPTION OF THE DRAWING

The single FIGURE is a schematic illustration of a computed tomography apparatus constructed and operating in accordance with the principles of the present invention.

DESCRIPTION OF THE PREFERRED EMBODIMENTS

The reference overall attenuation values for use in the inventive computed tomography apparatus can be determined either by computer simulation or by measurement. For the measurement, for example, one can proceed such as shown in the figure. This shows a CT scanner with an X-radiator 10 and a detector arrangement 12 that is composed of a number of detector cells 14 arranged side-by-side along a circular arc. The X-radiator 10 emits a fan-shaped X-ray beam in a plane. The detector cells 14 cover an overall projection region extending through the angular width of the beam fan, with each individual detector cell 14 detecting the intensity of the incident X-rays in the partial projection region it respectively covers. Each cell 14 supplies a corresponding measured intensity signal to an electronic evaluation and reconstruction unit 16. The X-radiator 10 and the detector arrangement 12 can be moved in a direction on normal to the fan plane without rotation along an axis 18.

Two wedges 20 and 22, respectively composed of different one of the two reference materials, are situated in the beam path. The wedges 20, 22 are arranged such that the thickness of the wedge 20 increases along the axis 18 and the thickness of the wedge 22 increases along the direction of the fan angle. When the X-radiator 10 and the detector arrangement 12 are displaced along the axis 18, measured values are obtained for a number of different thickness value pairs of the two reference materials. Using these measured values, the evaluation and reconstruction unit 16 then calculates the reference overall attenuation values. These indicate the actual attenuation affected with beam hardening that the X-rays experiences for the respective thicknesses of the two reference materials. In order to compensate individual errors of the detector cells 14, it is recommended to also scan the wedge 22 once with a thickness gradient inverted along the fan angle direction, this being indicated in broken lines at 22'.

After the reference overall attenuation values are determined with the measuring structure according to the figure or by simulation, one of the reference overall attenuation values $g_{ref}(s_1, s_2)$ can be unambiguously allocated to each pair of individual attenuation values $s_1$ and $s_2$ (potentially with the assistance of interpolations). The individual attenuation values $s_1$, $s_2$ thereby respectively reference the theoretical linear attenuation that the X-rays would experience in case of energy-independent absorption in the first and second reference material. They are linked with the thickness of the material via the following relationship:

$$s_{1,2} = d_{1,2} \cdot \mu_{1,2} \quad (6),$$

wherein $d_{1,2}$ is the thickness of the first material or the second reference material and $\mu_{1,2}$ is an absorption coefficient of the first or the second reference material that is effective for linear attenuation.

Moreover, a reference attenuation error $e_{ref}(s_1, s_2)$ can then also be unambiguously allocated to each pair of individual attenuation values $s_1$ and $s_2$, this deriving according to the following equation $$e_{ref}(s_1, s_2) = s_1 + s_2 - g_{ref}(s_1, s_2) \quad (7)$$

from the difference between the sum of the individual attenuation values $s_1$ and $s_2$ and the appertaining reference overall attenuation value $g_{ref}(s_1, s_2)$. This reference attenuation error $e_{ref}(s_1, s_2)$ represents the beam hardening error by which the reference overall attenuation value $g_{ref}(s_1, s_2)$ is lower than the sum of the individual attenuation values $s_1$ and $s_2$ as a consequence of beam hardening.

In an analogous way, the other individual attenuation value $s_2$ or $s_1$ can be unambiguously determined for each pair of a reference overall attenuation value $g_{ref}(s_1, s_2)$ and one of the individual attenuation values $s_1$ and $s_2$. The appertaining reference attenuation error $e_{ref}(s_1, s_2)$ then can also be unambiguously determined.

The above considerations are utilized in the invention in order to find the respectively correct correction value during operation of the CT scanner given examination of a patient. In the first version of the invention, the two respectively identified attenuation values $t_1$ and $t_2$ are employed as parameters therefor; in the second version, one identified attenuation value t and the overall attenuation value g are employed. When $s_1=t_1$ and $s_2=t_2$ are set in the first version, then an appertaining reference overall attenuation value $g_{ref}(s_1=t_1, s_2=t_2)$ and thus an appertaining reference attenuation error $e_{ref}(s_1=t_1, s_2=t_2)$, thus can be immediately unambiguously determined. The value of this reference attenuation error is then employed as correction value $k(t_1, t_2)$, i.e.

$$k(t_1, t_2) = e_{ref}(s_1 = t_1, s_2 = t_2) \quad (8)$$
$$= t_1 + t_2 - g_{ref}(s_1 = t_1, s_2 = t_2)$$

The comparable case applies given the second version of the invention. When $s_1=t$ and $g_{ref}(s_1=t, s_2)$ are set therein, an appertaining individual attenuation value $s_2$, and thus an appertaining reference attenuation error $e_{ref}(g_{ref}=g, s_1=t)$, can be immediately unambiguously determined. The value of this reference attenuation error is then employed as correction value $k(g, t)$, i.e.

$$k(g, t) = e_{ref}(g_{ref} = g, s_1 = t) \quad (9)$$
$$= t + s_2 - g_{ref}(s_1 = t, s_2).$$

One or more gray scale value thresholds according to which the overall image is resolved into its various gray scale value regions can, for example, be defined in order to extract the partial images from the overall image. It has proven expedient when one of the two partial images in the first version, or the single partial image in the second version, essentially shows only bone substance that is present in the transirradiated region. In the first version, the correction value is then determined dependent on the re-projected bone attenuation and a further attenuation partial value acquired by re-projection, preferably of the soft tissue attenuation; whereas, in the second solution, the correction value is determined dependent on the re-projected bone attenuation and in the overall attenuation value. The re-projected attenuation partial values are preferably attenuation values that indicate the theoretical linear attenuation in the respective body substance. Details regarding how the attenuation partial values can be determined from the partial images by re-projection can be derived, for example, from the previously cited literature.

There are various possibilities regarding the concrete implementation of the beam hardening correction information in the inventive computed tomography apparatus. In the first version, the identified reference overall attenuation values $g_{ref}(s_1, s_2)$ can be stored in the form of a look-up table in a memory of the evaluation and reconstruction unit 16 dependent on the individual attenuation values $s_1$ and $s_2$. In this case, the evaluation and reconstruction unit 16 would also execute the arithmetic operation according to Equation (2) in order to obtain the correction value. Instead of the reference overall attenuation values, alternatively, the reference attenuation errors $e_{ref}(s_1, s_2)$ can be directly stored in table form in the evaluation and reconstruction unit 16 dependent on the individual attenuation values $s_1$ and $s_2$.

In the second version, a look-up table can be stored in the evaluation and reconstruction unit 16 that indicates the second individual attenuation value $s_2$ dependent on the first individual attenuation value $s_1$ and on the reference overall attenuation value $g_{ref}(s_1, s_2)$. So that the arithmetic operation according to Equation (4) need not be constantly carried out by the evaluation and reconstruction unit 16, it is also possible to directly store the reference attenuation errors $e_{ref}(s_1, s_2)$ in table form in the evaluation and reconstruction unit 16 dependent on the reference overall attenuation value $g_{ref}(s_1, s_2)$ and on the first individual attenuation value $s_1$.

In an optional embodiment of the first version, a function u(x) that is dependent on a variable x can be determined for the determination of the beam hardening correction information, this function allocating a function value u(x) to every value of x, with $$x = A(Bs_1 + Cs_2) \quad (10)$$

this function value u(x) at least approximately corresponds to the difference between the sum of the respective, two individual attenuation values and the respective reference overall attenuation value, whereby A, B and C are constants. The evaluation and reconstruction unit 16 is configured for determining the correction value according to the following equation:

$$k(t_1, t_2) = u(x = A(Bt_1 + Ct_2)) \quad (11)$$

The linear combination according to Equation (10) makes it possible to reduce the dependency of the correction value $k(t_1, t_2)$ on two parameters to the dependency on one parameter. The constants A, B and C are defined such that the error between the reference attenuation error $e_{ref}(s_1=t_1, s_2=t_2)$ and the function value $u(x=A(Bt_1+Ct_2))$ becomes optimally small.

In an optional embodiment of the second version, analogously, a function v(y) dependent on a variable y can be determined for the determination of the beam hardening correction information, this function allocating a function value v(y) to each value of y, with $$y = D(Eg_{ref} + Fs_1) \quad (12)$$

The function value v(y) at least approximately corresponds to the difference between the sum of the respective, two individual attenuation values and the respective reference overall attenuation value, whereby D, E and F are constants. The evaluation and reconstruction unit is configured for determining the correction value according to the following equation:

$$k(g, t) = v(y = D(Eg + Ft)) \quad (13)$$

The constants D, E and F are defined in this case such that the error between the reference attenuation error $e_{ref}(g_{ref}=g, t_1, s_1=t)$ and the function value $v(y=D(Eg+ft))$ becomes optimally small.

The two functions u(x), v(y) either can be implemented as a look-up table in the evaluation and reconstruction unit 16 or in the form of a mathematical algorithm, insofar as a suitable approximation equation for the function u(x) or v(y) can be found.

It is self-evident, moreover, that not only the calibration measurements for the determination of the reference overall attenuation values can be implemented at the CT scanner shown in the figure, but also that the patient examination can ensue in the scanner when, additionally, a rotation of the radiator 10 and the detector arrangement 12 (insofar as this is not fashioned as ring detector) is provided in the direction of the fan angle.

It should be noted that it is possible without further difficulty to correct the overall attenuation values acquired in the examination of a patient a priori with the assistance of a standard algorithm, and to reconstruct the overall image from the overall attenuation values corrected in this way. The retrospectively determined correction values then will either be added to the original, non-corrected overall attenuation values, or the correction values will be reduced by the amount of the standard correction.

Although modifications and changes may be suggested by those skilled in the art, it is the intention of the inventors to embody within the patent warranted hereon all changes and modifications as reasonably and properly come within the scope of their contribution to the art.

We claim as our invention:

1. An X-ray computed tomography apparatus comprising:

a radiator/detector arrangement that supplies respective sets of measured intensity values for X-ray projections of a body slice of a patient, each measured intensity value of each set representing an intensity of the X-rays after penetration of the body slice in a partial projection region of an overall projection region; and an electronic evaluation and reconstruction unit connected to the radiator/detector arrangement for a) determining an overall attenuation value for each of the measured intensity values, said overall attenuation value representing an actual overall attenuation of the X-rays in the body slice in the appertaining partial projection region;

b) reconstructing an overall image of the body slice proceeding from the overall attenuation values;

c) extracting a first partially image of a first substance of the body slice from said overall image;

d) determining a respective first attenuation partial value from said first partial image for each partial region of the respective X-ray projection, each first attenuation partial value being a criterion for attenuation of the X-rays in the appertaining projection partial region in the first substance of the body slice, and allocating said first attenuation partial value to the overall attenuation value of the corresponding partial region;

e) extracting a second partial image from said overall image of a second substance in the body slice;

f) determining a respective second attenuation partial value from said second partial image for each partial region of the respective X-ray projection, each second attenuation partial value being a criterion for attenuation of the X-rays in the appertaining projection partial region in the second substance of the body slice, and allocating said second attenuation partial value to the overall attenuation value of the corresponding partial region;

g) determining a correction value for each overall attenuation value from the first and second attenuation partial values from predetermined beam-hardening correction information stored in the evaluation and reconstruction unit;

h) determining an overall attenuation value corrected for beam hardening for each overall attenuation value according to the equation:

$$g_{corr}=g+k(t_1, t_2)$$

wherein $g_{corr}$ is the overall attenuation value corrected for beam hardening, g is the overall attenuation value, $t_1$ is the first attenuation partial value, $t_2$ is the second attenuation partial value and $k(t_1, t_2)$ is the correction value determined from $t_1$ and $t_2$, and for determining the correction value $k(t_1, t_2)$, said evaluation and reconstruction unit
  i) determining a set of reference overall attenuation values $g_{ref}(s_1, s_2)$ for a material sequence composed of a first reference material and a second reference material different therefrom for different thickness combinations, each reference overall attenuation value $g_{ref}$ of the set representing the overall attenuation of the X-rays for a specific thickness combination of the material sequence;
  j) calculating a theoretical linear attenuation of the X-rays for each thickness of the first reference material from the thickness combinations of the material sequence represented by a first individual attenuation value $s_1$;
  k) calculating a theoretical linear attenuation of the X-rays for each thickness of the second reference material from the thickness combinations of the material sequence represented by a second individual attenuation value $s_2$; and
  l) determining the correction value for each thickness combination of the material sequence according to the equation $$k(t_1, t_2)=t_1+t_2-g_{ref}(s_1=t_1, s_2=t_2),$$

wherein $g_{ref}(s_1=t_1, s_2=t_2)$ is the reference overall attenuation value for a thickness combination of the material sequence for which $s_1=t_1$ and $s_2=t_2$.

2. A computed tomography apparatus as claimed in claim 1 wherein the evaluation and reconstruction unit extracts substantially only image parts of the overall image that correspond to a bone structure in the body slice in one of the two partial images.

3. A computed tomography apparatus as claimed in claim 2 wherein the evaluation and reconstruction unit extracts substantially only image parts of the overall image that correspond to a soft tissue substance in the body slice in the other of the two partial images.

4. A computed tomography apparatus as claimed in claim 1 wherein, for determining the beam hardening correction information, the evaluation and reconstruction unit stores a function u(x) dependent on a variable x, which allocates a function value u(x) to each value of x, with $$x=A(Bs_1+Cs_2),$$

said function value substantially corresponding to a difference between a sum of the respective, two individual attenuation values and the respective reference overall attenuation value, wherein A, B and C are constants; and wherein the evaluation and reconstruction unit determines the correction value according to the equation:

$$k(t_1, t_2)=u(x=A(Bt_1+Ct_2)).$$

5. An X-ray computed tomography apparatus comprising:
a radiator/detector arrangement that supplies respective sets of measured intensity values for X-ray projections of a body slice of a patient under examination, each measured intensity value of the set representing an intensity of X-rays after penetration of the body slice in a partial projection region of an overall projection region; and
an electronic evaluation and reconstruction unit connected to the radiator/detector arrangement for
  a) determining an overall attenuation value for each of the measured intensity values, said overall attenuation value representing an actual overall attenuation of the X-rays in the body slice in the appertaining partial projection region;
  b) reconstructing an overall image of the body slice proceeding from the overall attenuation values;
  c) extracting a partial image of a selected substance of the body slice from said overall image;
  d) determining an attenuation partial value from said partial image for each partial region of the respective X-ray projection, said attenuation partial value being a criterion for the attenuation of the X-rays in the appertaining projection partial region in the selected substance of the body slice, and allocating said attenuation partial value to the overall attenuation value of the corresponding partial region;
  e) determining a correction value for each overall attenuation value from the attenuation partial value from predetermined beam-hardening correction information stored in the evaluation and reconstruction unit;
  f) determining an overall attenuation value corrected for beam hardening for each overall attenuation value according to the equation:

$$g_{corr}=g+k(t)$$

wherein $g_{corr}$ is the overall attenuation value corrected for beam hardening, g is the overall attenuation value, t is the attenuation partial value, and k(t) is the correction value determined from t, and, for determining the correction value k(t), said evaluation and reconstruction unit
  g) determining a set of reference overall attenuation values for a material sequence composed of a first reference material and a second reference material different therefrom for different thickness combinations, each reference overall attenuation value $g_{ref}$ of the set representing the overall attenuation of the X-rays for a specific thickness combination of the material sequence;
  h) calculating a theoretical linear attenuation of the X-rays for each thickness of the first reference material from the thickness combinations of the material sequence represented by a first individual attenuation value $s_1$;
  i) calculating a theoretical linear attenuation of the X-rays for each thickness of the second reference material from the thickness combinations of the material sequence represented by a second individual attenuation value $s_2$; and
  j) determining the correction value for each thickness combination of the material sequence according to the equation $$k(g, t)=t+s_2-g_{ref}(s_1=t, s_2),$$

wherein $g_{ref}(s_1=t, s_2)$ is the reference overall attenuation value for a thickness combination of the material sequence for which $s_1=t$ given $s_2$ and, for which $$g_{ref}(s_1=t, s_2).$$

6. A computed tomography apparatus as claimed in claim 5 wherein, for determining the beam hardening correction information, the evaluation and reconstruction unit stores a function v(y) dependent on a variable y which allocates a function value v(y) to each value of y, with $$y=D(Eg_{ref}+Fs_1),$$

said function value substantially corresponding to a difference between a sum of the respective, two individual attenuation values and the respective reference overall attenuation value, wherein D, E and F are constants, and wherein the evaluation and reconstruction unit determines the correction value according to the equation $$k(g, t)=v(y=D(Eg+Ft)).$$

7. A computed tomography apparatus as claimed in claim 5 wherein the evaluation and reconstruction unit extracts substantially only image parts of the overall image that correspond to a bone structure in the body slice in said partial image.

* * * * *